United States Patent
Holm et al.

(10) Patent No.: US 10,406,320 B1
(45) Date of Patent: Sep. 10, 2019

(54) SYSTEMS AND METHODS FOR SHEATH RETRACTION

(75) Inventors: Brian C. Holm, Mountain View, CA (US); Shane P. Rogers, San Jose, CA (US); Justin W. Sokel, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 934 days.

(21) Appl. No.: 13/584,316

(22) Filed: Aug. 13, 2012

Related U.S. Application Data

(60) Provisional application No. 61/524,266, filed on Aug. 16, 2011.

(51) Int. Cl.
*A61M 25/01* (2006.01)
*A61F 2/966* (2013.01)
*A61M 25/06* (2006.01)

(52) U.S. Cl.
CPC ............ *A61M 25/01* (2013.01); *A61F 2/966* (2013.01); *A61M 2025/0681* (2013.01)

(58) Field of Classification Search
CPC .......... A61M 25/0618; A61M 25/0662; A61M 25/0668; A61M 2025/0675; A61M 2025/0681; A61F 2/97; A61F 2/966; A61F 2/2436; A61F 2/962
USPC ........................................................ 604/163
See application file for complete search history.

(56) References Cited

U.S. PATENT DOCUMENTS

| | | | |
|---|---|---|---|
| 5,647,857 A * | 7/1997 | Anderson | A61F 2/958 604/160 |
| 2002/0151953 A1* | 10/2002 | Chobotov | A61F 2/0095 623/1.11 |
| 2005/0085842 A1* | 4/2005 | Eversull | A61F 2/966 606/191 |
| 2005/0090779 A1* | 4/2005 | Osypka | A61M 25/0097 604/160 |
| 2009/0024133 A1* | 1/2009 | Keady | A61F 2/95 606/99 |
| 2011/0034987 A1* | 2/2011 | Kennedy | A61F 2/95 623/1.11 |

* cited by examiner

*Primary Examiner* — Emily L Schmidt

(57) ABSTRACT

A medical device delivery system includes a sock removal mechanism, which also locks a deployment handle. The ability to lock the handle allows a medical device to be safely and effectively deployed to a treatment site without prematurely deploying a medical device. The sock can cover and/or restrain the medical device. The sock removal mechanism can release and retract the sock when separated from the handle.

4 Claims, 8 Drawing Sheets

SYSTEMS AND METHODS FOR SHEATH RETRACTION

CROSS REFERENCE RELATED APPLICATIONS

This Patent Application claims priority to and the benefit of Provisional Patent Application Ser. No. 61/524,266 filed on Aug. 16, 2011, the content of which is incorporated by reference herein in its entirety.

BACKGROUND

Field

The invention relates to improved medical device delivery systems, and more specifically, to systems and methods for facilitating delivery of a medical device to a treatment region in the vasculature of a patient.

Discussion of the Related Art

Current methods for providing medical treatment to human vasculature involve the use of catheters. In many cases, catheters are used to deliver medical devices to areas of a patient's vasculature. These devices include medical devices, such as, for example, stents and stent grafts (self-expanding or otherwise), bifurcated stents and stent grafts, drug-eluting stents, vascular filters, such as inferior vena cava filters, as well as endoluminal imaging devices.

Medical device delivery systems generally comprise a handle, a catheter having a proximal end and a distal end, a medical device located at the distal end of the catheter. Various medical devices may also include a sheath or "sock" that protects the medical device and the vasculature as the device is delivered to the treatment region. For example, the sock may prevent the medical device from becoming contaminated as the medical device delivery system is navigated to the treatment region. The sock must be removed once the medical device reaches the treatment region so that the medical device can be appropriately deployed.

The handles of various medical device delivery systems may comprise one or more moveable components that are configured to provide an input through the catheter to the medical device. For example, the moveable components may be used to deploy a medical device at a treatment region. One significant problem with current medical device delivery systems is the ability to inadvertently provide an input to a moveable component. This inadvertent input may cause a device to deploy prematurely. The premature deployment may cause damage to the vasculature or require that another procedure be performed to deliver the medical device to the intended treatment region.

Thus, a need exists for medical device delivery systems that can safely and effectively deliver medical devices to the treatment region within the patient's vasculature and prepare the medical devices for deployment. Those skilled in the art will recognize numerous advantages of such exemplary embodiments over the prior art, including, for example, removing the sock and reducing the likelihood of inadvertent deployment of a medical device.

DETAILED DESCRIPTION

Figure 1:
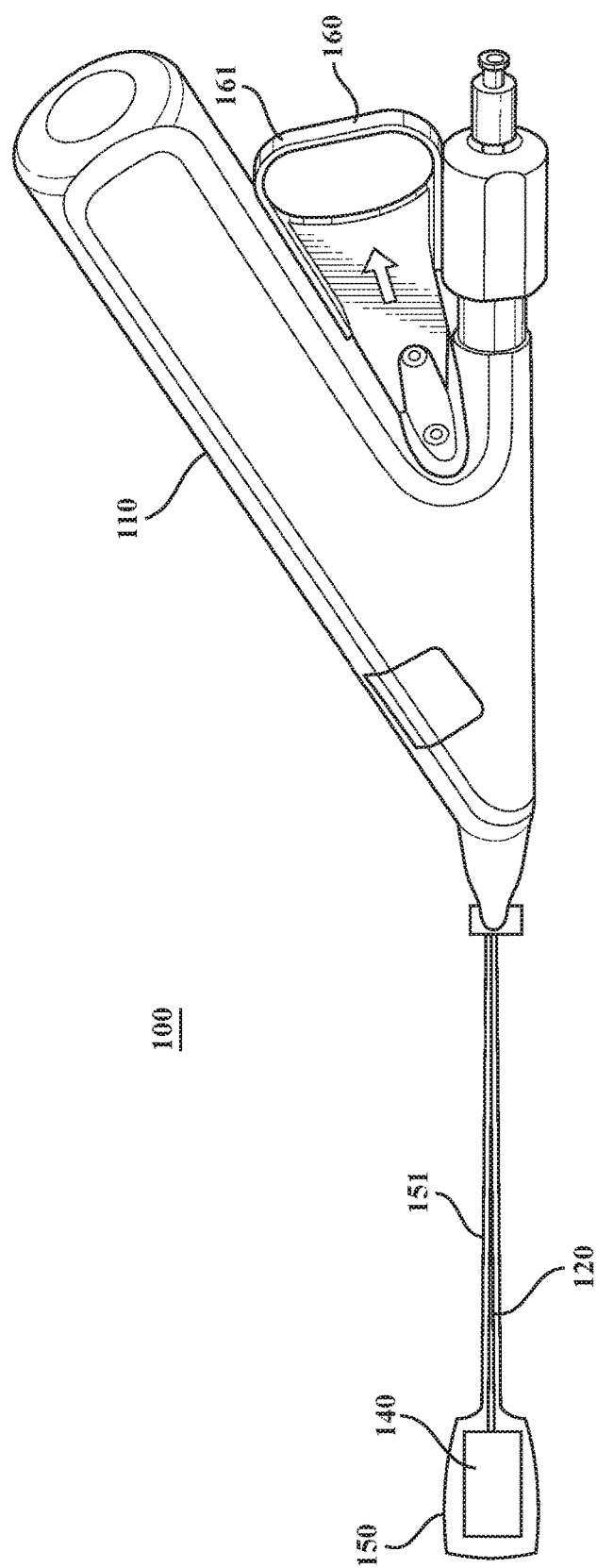
FIG. 1 illustrates a profile view of an exemplary medical device delivery system.
Figure 2A:
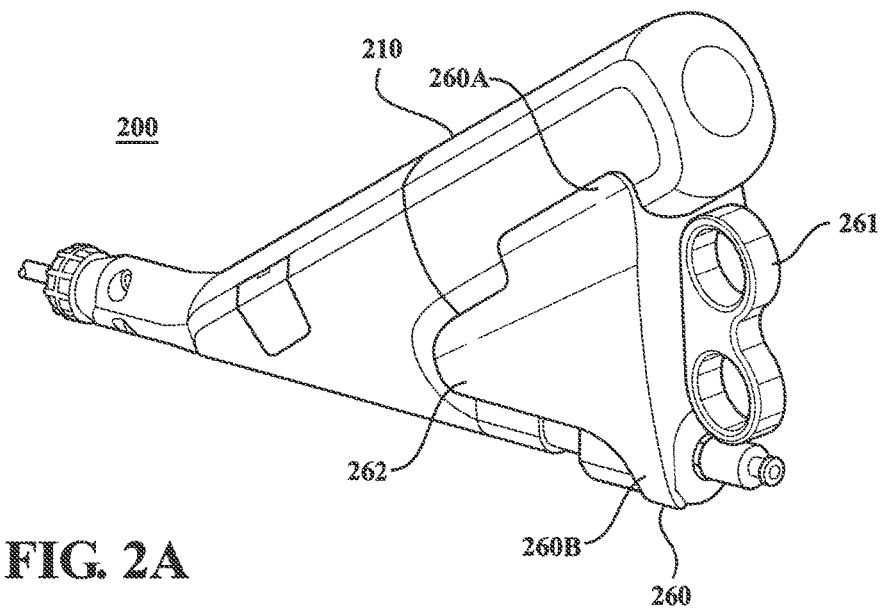
FIGS. 2A-2E illustrate various views of an exemplary handle system comprising a rotatable activation handle and associated components in accordance with various embodiments.
Figure 2B:
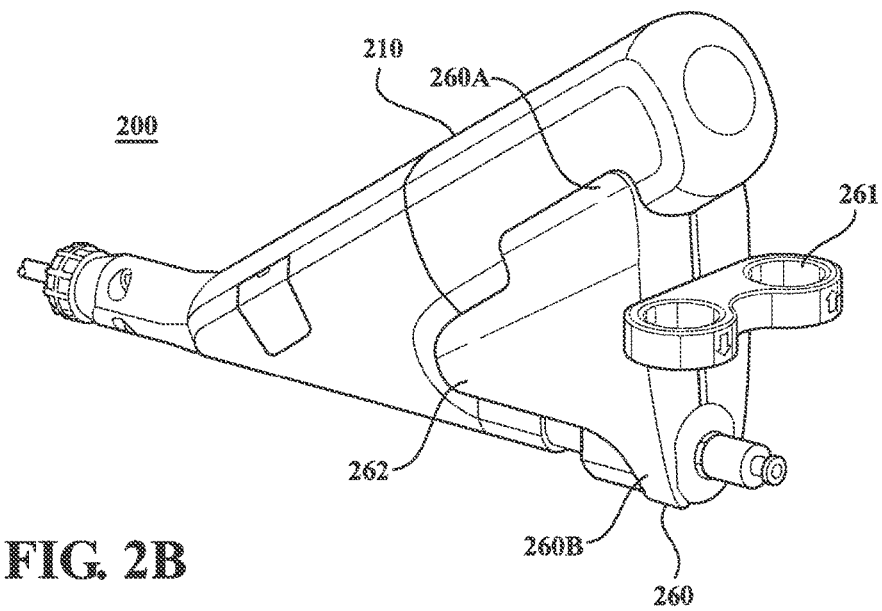
Figure 2C:
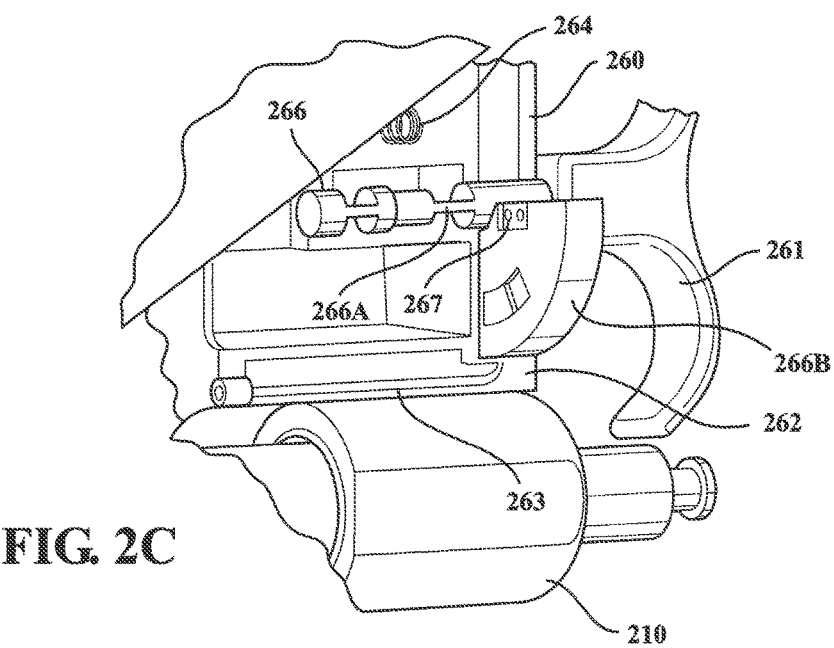
Figure 2D:
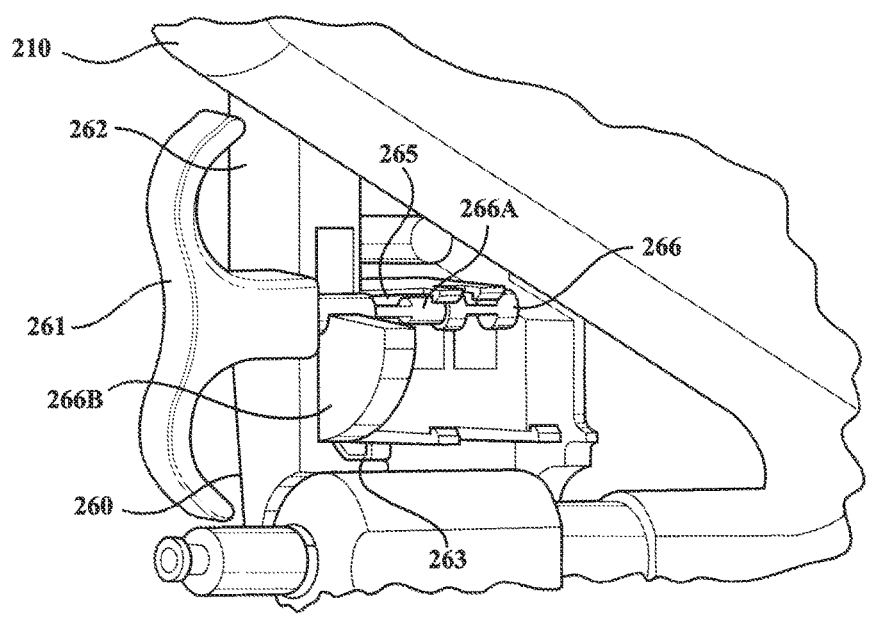
Figure 2E:
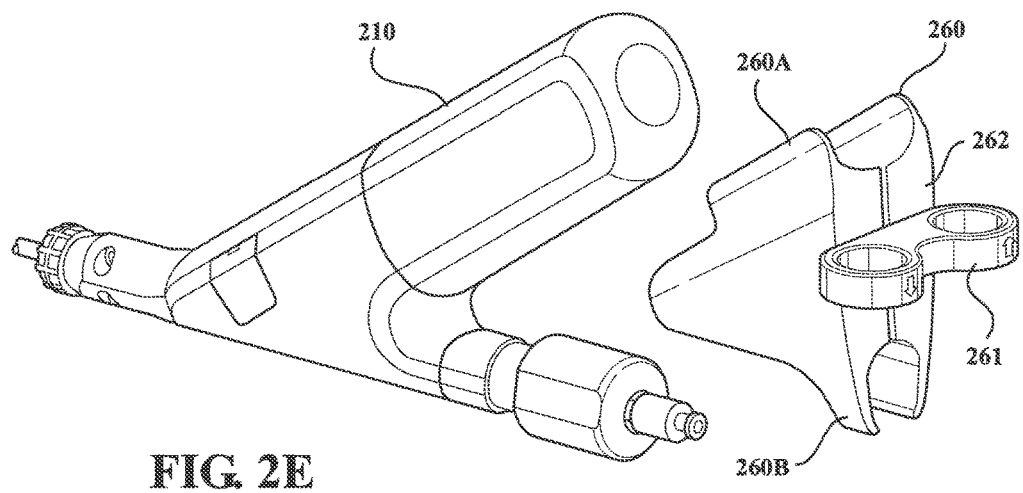

The detailed description of various embodiments herein makes reference to the accompanying drawing figures, which show various embodiments and implementations thereof by way of illustration and best mode, and not of limitation. While these embodiments are described in sufficient detail to enable those skilled in the art to practice the embodiments, it should be understood that other embodiments may be realized and that mechanical and other changes may be made without departing from the spirit and scope of the present disclosure. Furthermore, any reference to singular includes plural embodiments, and any reference to more than one component may include a singular embodiment. Moreover, recitation of multiple embodiments having stated features is not intended to exclude other embodiments having additional features or other embodiments incorporating different combinations of the stated features. In describing various exemplary embodiments, the term distal is used to denote the end of an exemplary device nearest to the treatment region within a patient's body. The term proximal is used to denote the end of an exemplary device nearest to the user or operator of the device.

The present disclosure describes a number of non-limiting, exemplary embodiments, each of which may be used alone or in coordination with one another. An exemplary medical device delivery system may comprise a handle, a catheter, and a medical device. A medical device delivery system may further comprise a sock removal mechanism, an introducer sheath, and a sock. In such embodiments, the catheter and introducer sheath may couple to the handle, such that an input at the handle causes a response at least one of the introducer sheath and catheter. The introducer sheath may house the catheter. The medical device may be situated at the distal end of the catheter, outside of the introducer sheath. The sock removal mechanism may couple to the handle and may lock the handle in an inoperable position, such that the handle may not receive an input until the sock removal mechanism is removed. The sock may surround the catheter within the introducer sheath. The sock may further exit the distal end of the introducer sheath and cover the medical device. In exemplary embodiments, the outer diameter of the introducer sheath may be less than or substantially equal to the outer diameter of the medical device in its collapsed and/or compressed configuration.

In various exemplary embodiments, a medical device delivery system may be any suitable system configured to deliver a medical device at a treatment region. In these embodiments, at least a portion of catheter, introducer sheath, medical device, sock, and release of medical device delivery system enter the vasculature of a patient at an incision or crossing to locate medical device at a treatment region. Prior to proper positioning in a treatment region, sock removal mechanism may lock medical device delivery system, such that medical device may not be actuated, released, un-restrained, or otherwise deploy. In an embodiment and upon reaching the treatment site, sock removal mechanism may actuate causing release to unrestrain the distal end of sock and remove sock to deploy medical device.

In an exemplary embodiment and with reference to FIG. 1, medical device delivery system 100 is shown. In this embodiment, handle 110 couples to catheter 120 and an introducer sheath at the distal end of handle 110. Catheter 120 and/or introducer sheath may removably couple to medical device 140. Sock 150 covers and/or retains medical device 140 in a compressed and/or constrained configuration. The compressed and/or constrained configuration allows medical device 140 to travel through the vasculature to the treatment region. Handle 110 may also couple to sock removal mechanism 160. In various embodiments, sock removal mechanism 160 facilitates the removal of sock 150 and/or may lock handle 110, preventing deployment or other movement of medical device 140 prior to reaching the treatment region.

In an embodiment, medical device delivery system 100 may further comprise a release 151. Release 151 may include any suitable structure including a suture, a clip and tether, and/or the like (not shown). At least a portion of release 151 may travel within the introducer sheath. Release 151 may couple to the distal end of sock 150. Release 151 may also couple to sock removal mechanism 160. In an embodiment, sock 150 may also couple to sock removal mechanism 160. Upon actuation of sock removal mechanism 160 and separation of sock removal mechanism 160 from handle 110, release 151 may open the distal end of sock 150. After the distal end of sock 150 opens, sock removal mechanism 160 may be further separated from handle 110, causing sock 150 to be retracted toward the proximal end of medical device delivery system 100. The retraction of sock 150 may facilitate the deployment of medical device 140.

In various embodiments, sock 150 may also be retractable and/or removable from medical device delivery system 100 without a release structure. For example, the distal end of sock 150 may be retained, closed, or otherwise configured to taper to a diameter smaller than that of medical device 140 without additional structure or devices (such as sutures, clips, tethers, or the like). For example, sock 150 may have a tapered and/or gathered distal end that is heat formed (e.g., shrunk) or otherwise manufactured in sock 150. The tapered distal end may have enough flexibility to expand around medical device 140 to facilitate the removal of sock 150. In such embodiments, when sock removal mechanism 160 is separated from handle 110, the tapered distal end of sock 150 is pulled and expanded around medical device 140, such that sock 150 is retracted over or removed from medical device 140. Thus, sock 150 can be removed in as little as one motion of sock removal mechanism 160.

In an exemplary embodiment, handle 110 may be any suitable mechanism configured to receive an input and communicate that input to another mechanism. Handle 110 may comprise one or more movable and/or rotatable components. In an embodiment, handle 110 may receive one or more inputs from a user. Handle 110 may also be lockable. In an embodiment, handle 110 may removably couple to sock removal mechanism 160.

In an embodiment, catheter 120 may be a flexible element having proximal and distal ends and capable of passing through a lumen of the vasculature. Examples include a guidewire, catheter, optical fiber, or the like. Catheter 120 may comprise a lumen over the entire distance or a part thereof or may be solid throughout. Catheter 120 may comprise a blunt, rounded, or tapered distal tip, to name a few, and may be characterized by varying degrees of rigidity or softness, which may further vary along the length of the elongate member. Catheter 120 may removably couple to, receive, retain, and/or position one or more devices, including, for example, an medical device, a deployment sheath, a sock, a retaining mechanism, a spacer, a marker, a device configured to emit light, a device configured to capture images and/or video, and/or the like. Catheter 120 may have any cross-sectional shape including circular, oval, triangular, square, polygon shaped or randomly shaped. An exemplary catheter 120, or any portion thereof, can be hydrophilic or hydrophobic. Additionally, catheter 120, or any portion thereof, can be comprised of any number of materials including silicone, latex, polyurethanes, polyvinyl chlorides, polyethylenes, polysiloxanes, polycarbonates, nylons, fluoropolymers such as PTFEs, stainless steel, nitinol, or any other biocompatible material, including combinations of the foregoing.

In an exemplary embodiment, the introducer sheath may be a flexible element having proximal and distal ends and capable of passing through a lumen of the vasculature. Examples include a catheter, optical fiber, or the like. The introducer sheath may comprise a lumen over the entire distance or a part thereof or may be solid throughout. The introducer sheath may comprise a blunt, rounded, or tapered distal tip, to name a few, and may be characterized by varying degrees of rigidity or softness, which may further vary along the length of the elongate member. The introducer sheath may removably couple, receive, retain, and/or position one or more devices, including, for example, a medical device, a deployment sheath, a sock, a retaining mechanism, a spacer, a marker, a device configured to emit light, a device configured to capture images and/or video, and/or the like. The introducer sheath may have any suitable diameter. In one embodiment, the introducer sheath may have a diameter that is less than or substantially equal to a device. The introducer sheath may have any cross-sectional shape including circular, oval, triangular, square, polygon shaped or randomly shaped. An introducer sheath, or any portion thereof, can be hydrophilic or hydrophobic. Additionally, an introducer sheath, or any portion thereof, can be comprised of one or more materials including silicone, latex, polyurethanes, polyvinyl chlorides, polyethylenes, polysiloxanes, polycarbonates, nylons, fluoropolymers such as PTFEs, stainless steel, nitinol, or any other biocompatible material, including combinations of the foregoing.

Catheter 120 may be insertable within the introducer sheath. Catheter 120 may be insertable in the introducer sheath at the time of assembly of medical device delivery system 100. Catheter 120 may also be insertable in introducer sheath 130 after the introducer sheath has been positioned in the vasculature. In an embodiment, catheter 120 may be inserted within the introducer sheath and coupled to a device. As noted above, the device may have a diameter that is greater than or substantially equal to the diameter of the introducer sheath. In this embodiment, catheter 120 and the introducer sheath are assembled prior to introduction of medical device delivery system 100 into the vasculature.

In an exemplary embodiment, medical device 140 comprises any device or structure configured to provide and/or support a therapeutic use in a vasculature. In various embodiments, medical device 140 may be any medical device that may be covered or constrained with a sock and/or sheath and delivered endovascularly. For example, a stent or stent graft, when implanted endovascularly, must be constrained to a low delivery profile in order to gain access to the treatment site. Similarly, fillers, valves, bifurcated stents, occluders, drug-delivering devices, such as drug-eluting balloons and stents, oncology therapies, pressure flow monitors, energy transmission devices, spacers, optical devices, markers and/or other similar devices may also be covered with a sock and/or sheath and delivered endovascularly. In the case of devices that deliver a drug or other therapeutic agent, the covering may also ensure minimal drug release into the bloodstream during delivery.

In an embodiment, sock removal mechanism 160 may be any system suitably configured to lock handle 110 and prepare medical device 140 for deployment. Sock removal mechanism 160 may also comprise one or more stops that prevent one or more movable pieces of handle 110 from moving or rotating when sock removal mechanism 160 is coupled to handle 110. These stops may be any suitable structure configured to prevent movement and/or rotation, including, for example, a tab, a collar, a flat, a pin, a fastener, such as a setscrew, or any other suitable device.

Sock 150 and release 151 may operatively couple to sock removal mechanism 160. In an embodiment, sock removal mechanism 160 may comprise activation handle 161. When engaged by a user, activation handle 161 may be configured to separate sock removal mechanism 160 from handle 110. The separation may also cause sock 150 and release 151 to retract toward the proximal end of medical device delivery system 100.

In an exemplary embodiment and with reference to FIGS. 2A-2E, handle 210 of medical device delivery system 200 may couple to sock removal mechanism 260. Sock removal mechanism 260 may be any system suitably configured to lock handle 210. For example, sock removal mechanism may comprise a first portion 260A and a second portion 260B. First potion 260A may receive and retain a first rotatable portion of handle 210, also referred to herein as a movable component. Similarly, second portion 260B may receive and retain a second rotatable portion of handle 210. The ability to lock handle 210 enables a user to safely insert medical delivery system 300 in the vasculature of a patient and position the system at a treatment region without inadvertently deploying medical device 140.

Sock removal mechanism 260 may also be configured to prepare medical device for deployment. Sock removal mechanism 260 may comprise an activation handle 261 and a body 262. Activation handle 261 may couple to and/or install within body 262. In various embodiments, handle 261 may be moveable within body 262.

In another embodiment, body 262 may be any suitable device configured to removably install in and lock handle 210 with first portion 260A and second portion 260B. Body 262 may comprise or single piece or may be an assembly. In an embodiment, body 262 may be an assembly comprising a first half and a second half. Body 262 may define a channel 263. Body 262 may comprise a spring 264, and latches 265. The first half and the second half may removably couple to one another with one or more latches 265. The latches may be configured to couple the first half and the second half together such that a predetermined amount of force is must be applied to separate latch 265, and, as a result, separate the first half and the second half of body 262. Spring 264 may be installed in at least one of the first half and the second half. In this embodiment, spring 264 biases the first half apart from the second half. In such embodiments, spring 264 may have a spring force that is less than or substantially equal to the predetermined amount of force required to overcome latch 265.

In an embodiment, activation handle 261 may further comprise cam 266. At least a portion of cam 266 may install within body 262, such that activation handle 261 is rotatable with respect to body 262. In an embodiment, rotation of handle 261 may cause cam 266 to exert a force on latch 265 causing body 262 to separate. The separation of body 262 may also cause sock removal mechanism 260 to disengage from handle 210, such that sock removal mechanism 260 may be removed from handle 210. Cam 266 may comprise one of more portions of varying diameter. For example, cam 266 may comprise a first cam portion 266A having a first diameter of a suitable size and shape to install and rotate within a first cavity defined by body 262. Cam 266 may also comprise a second cam portion 266B having a second diameter that is larger than first diameter of first cam portion 266A and is configured to install and rotate within a second cavity defined by body 262.

With momentary reference back to FIG. 1, body 262 may be configured to receive sock 150. Sock 150 may be received at any suitable location. For example, sock 150 may enter body 262 through a hole defined by body 262. Sock 150 may travel through body 262 substantially unencumbered. Sock 150 may also couple to cam 266 at any suitable point. Referring back to FIG. 2, sock 150 is configured to couple to cam 266 at first cam portion 266A.

The first half of body 262 may at least partially define a channel 263. The second half body 262 may further define channel 263. Channel 263 may be of any suitable size and shape. When the first half and the second half of body 262 are assembled and/or coupled together by latch 265, the first half and the second half define channel 263. Channel 263 may receive release 151 and provide a path of travel for release 151. Moreover, channel 263 may provide a path configured to guide release 151 through body 262. Second cam portion 266B may further comprise a passage from channel 263 to an attachment point 267, for example, via a hole on an outer diameter of second cam portion 266B through which the release 151 may travel and anchor at attachment point 267.

In an embodiment and with continued concurrent reference to FIG. 1 and FIGS. 2A-2E, sock 150 and release 151 may be released and retracted from medical device 140. Rotation of activation handle 261 may exert a force on sock 150 and release 151, where both sock 150 and release 151 couple to cam 266 at various points. In one embodiment, where sock 150 couples to first cam portion 266A and release 151 couples to second cam portion 266B at attachment point 267, rotation of handle 261 may cause displacement of sock 150 and release 151. For example, the larger second diameter of second cam portion 266B displaces release 151 a significantly larger distance than negligible displacement of the sock 150. The greater movement of release 151 causes a suture (or other closure mechanism) closing the distal end of sock 150 to release. The release of the distal end of sock 150 allows both sock 150 and release 151 to be retracted from medical device 140 as sock removal mechanism 260 is separated from handle 210 in the proximal direction.

Figure 3A:
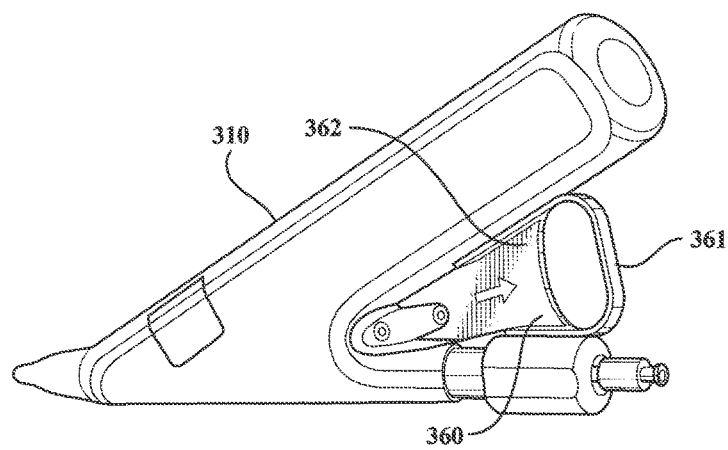
FIGS. 3A-3C illustrate various views of an exemplary handle system coupling to a sock removal mechanism at a nipple in accordance with various embodiments.
Figure 3B:
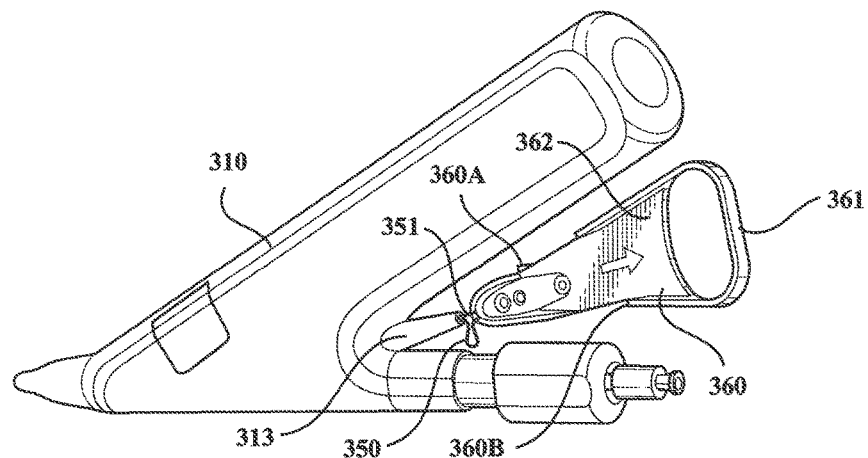
Figure 3C:
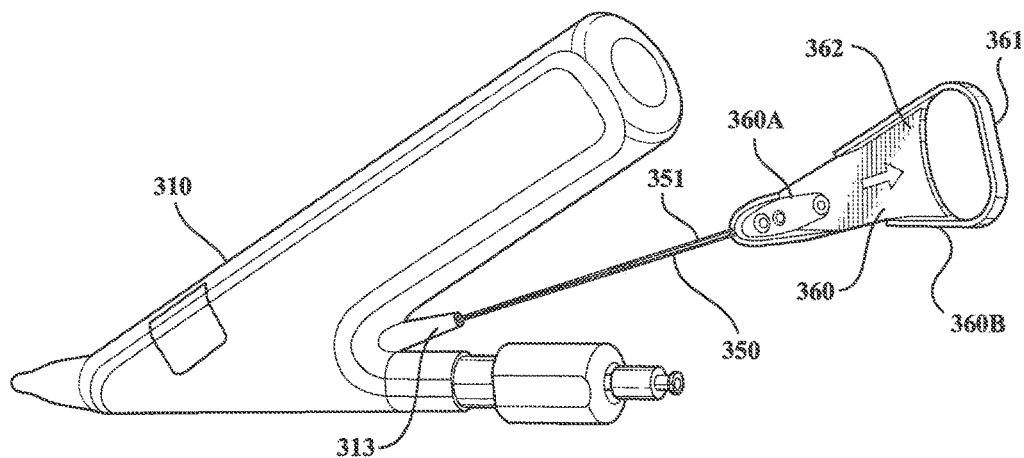
Figure 4A:
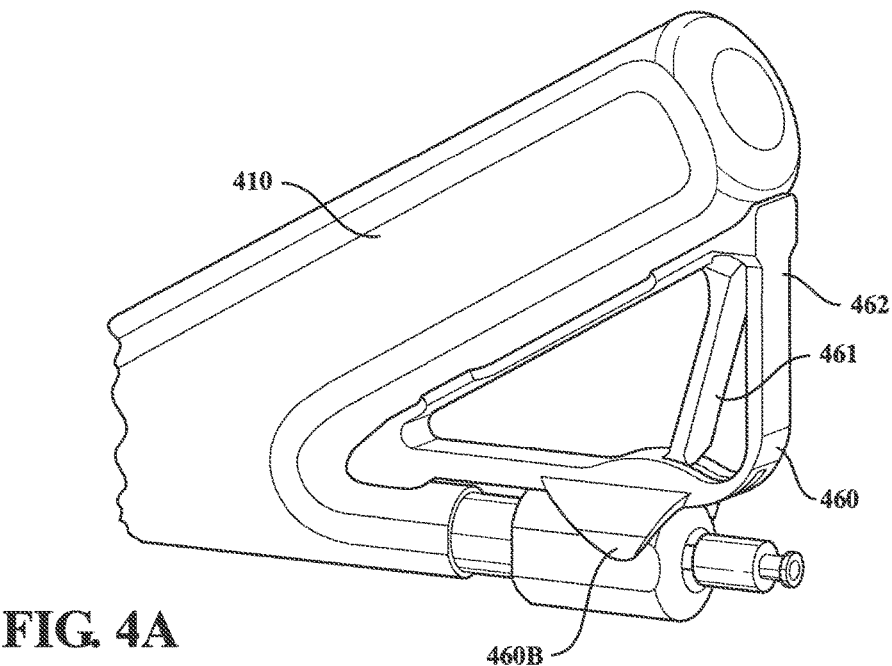
FIGS. 4A-4E illustrate various views of an exemplary handle system comprising a trigger and associated components in accordance with various embodiments.
Figure 4B:
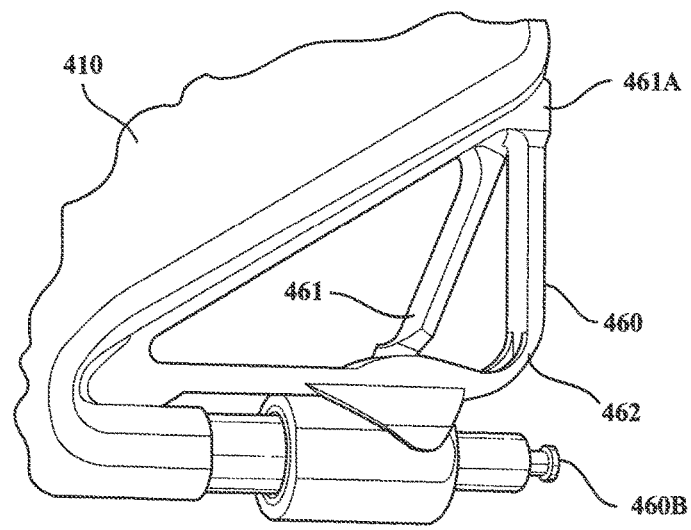
Figure 4C:
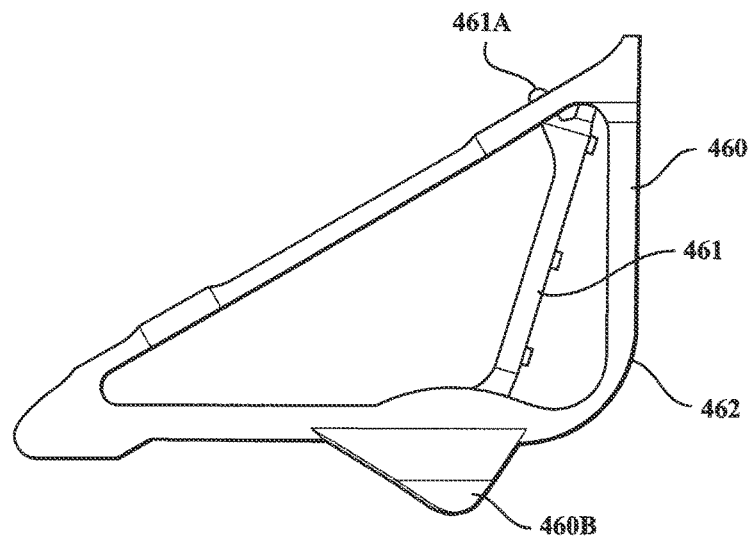
Figure 4D:
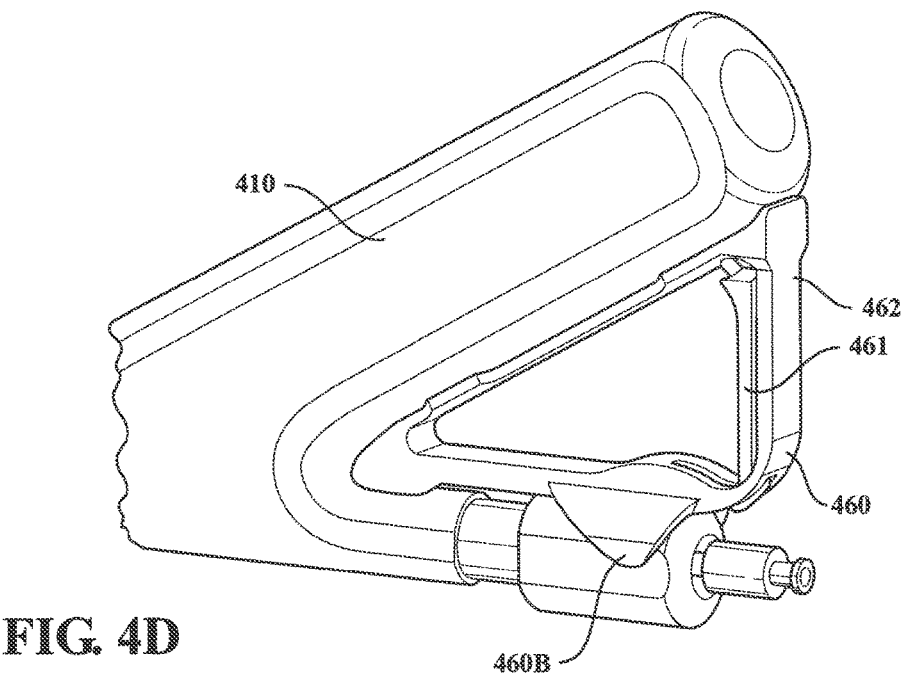
Figure 4E:
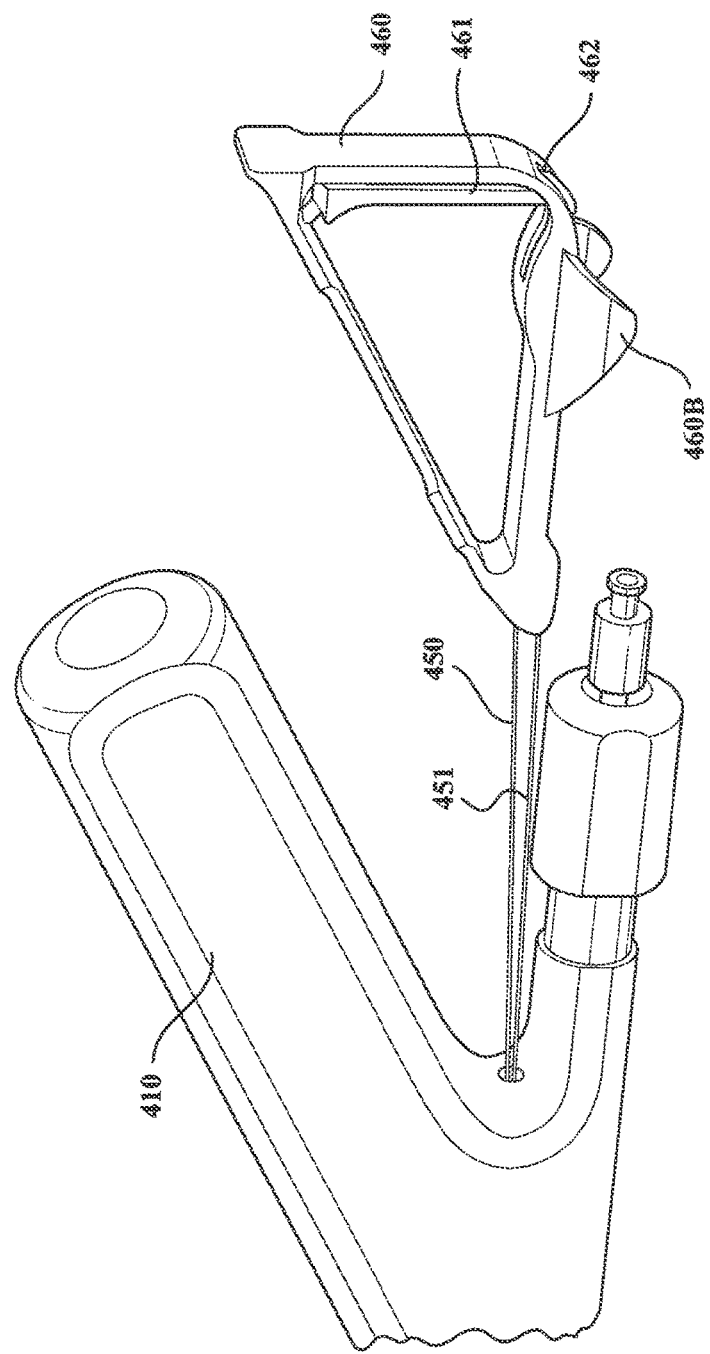

In an embodiment and with reference to FIGS. 3A-3C, sock removal mechanism 360 may be any suitable mechanism configured to removably couple to and lock handle 310. In an embodiment, sock removal mechanism 360 may be configured with a locking tab 360A and a flat 360B. Sock removal mechanism 360 may removably couple to handle 310 such that locking tab 360A secures and prevents movement and/or rotation of a first component of handle 310. Similarly, flat 360B of sock removal mechanism 360 may further couple to or contact an opposing flat of a second component of handle 310, such that flat 360B prevents movement or rotation of the second component.

In an exemplary embodiment, handle 310 may comprise a nipple 313. Nipple 313 may comprise a retention mechanism. Sock removal mechanism 360 may removably couple to nipple 313. Nipple 313 may also positively retain sock removal mechanism 360 at the retention mechanism. The retention mechanism of nipple 313 may be designed to exert a predetermined force on sock removal mechanism 360. This predetermined force may be greater than a force that could be applied to sock removal mechanism 360 by inadvertent jostling or contact, but still allow a user to detach sock removal mechanism 360 without unduly jarring medical device delivery system 100 when installed in the vasculature during a procedure.

In an embodiment, sock removal mechanism 360 may comprise an activation handle 361. Activation handle 361 may be any suitable structure configured for engagement by a user. In one embodiment, activation handle 361 may be suitably configured to be engaged by one or more fingers of a user to allow for comfortable, intuitive, stable operation of medical device delivery system 200.

Handle 310 may define a first passage between its distal end and nipple 313. Nipple 313 may define a second passage between the first passage and the environment. At least a portion of sock 350 may be threaded through the first passage and the second passage. A "slack portion" of sock 350 may also exit the second passage. Release 351 may also be threaded through the first passage and the second passage. Sock 350 and release 351 may couple to sock removal mechanism 360. Moreover, when sock removal mechanism 360 is coupled to handle 310, sock 350 and release 351 may be in tension with no slack present. For example, to facilitate this, the slack portion of sock 350 may be wrapped around or positioned against nipple 313 such that the slack portion is positively retained by sock removal mechanism 360, when sock removal mechanism 360 is installed on nipple 313. The retention of the slack portion by sock removal mechanism 360, prior to removal of sock removal mechanism 360 from handle 310 allows sock 350 to remain in tension.

In an embodiment, when sock removal mechanism 360 is removed from handle 310, as shown in FIG. 3B, the slack portion of sock 350 is freed. The slack portion may be any suitable length to allow release 351 sufficient travel to open the distal end of sock 350 prior to removal of sock 350. In an embodiment, as sock removal mechanism 360 detaches from nipple 313 and separates from handle 310, release 351 is pulled in tension and the slack portion of sock 350 is reduced. As sock removal mechanism 360 separates further from handle 310, the slack portion of sock 350 is completely reduced and sock 350 is pulled in tension. In tension, sock 350 is retracted from a medical device preparing it for deployment.

In an embodiment and with reference to FIGS. 4A-4E, sock removal mechanism 460 may couple to handle 410. Sock removal mechanism 460 may comprise a trigger 461 and a body 462. In one embodiment, sock removal mechanism 460 may comprise an engagement portion 460B and a tab 461A. Sock removal mechanism 460 may prevent one or more movable components of handle 410 from moving and/or rotating. For example, when coupled together, tab 461A of sock removal mechanism 460 may be received within a first movable component of handle 410. Tab 461A may prevent the first movable component from moving or otherwise rotating, until sock removal mechanism 460 is removed from handle 410. Similarly, engagement portion 460B may be engage, contact, or otherwise interface within a second movable component of handle 410. Engagement portion 460B may prevent the second movable component from moving or otherwise rotating, until sock removal mechanism 460 is removed from handle 410.

Handle 410 may define a first passage between its distal end and a surface of handle 410 that engages sock removal mechanism 460. Sock removal mechanism 460 may define a second passage between the first passage and trigger 461. At least a portion of sock 450 may be threaded through the first passage and coupled to sock removal mechanism 460 at any suitable point. Release 451 may be threaded through the first passage and the second passage. Release 451 may couple to trigger 461 at any suitable point, such that, release 451 is tensioned and moved when trigger 461 is actuated.

In another embodiment, release 451 may also be coupled to a displacement multiplier (not shown), which is coupled to trigger 461. The displacement multiplier may be housed with sock removal mechanism 460. The displacement multiplier may be any suitable structure configured to increase the displacement of release 451 relative to the displacement of trigger 461, when trigger 461 is actuated. This feature allows the stroke of trigger 461 to be shortened, thereby decreasing the overall package size of sock removal mechanism 460, while providing a sock removal mechanism with sufficient release 451 displacement to free the distal end of sock 450. The displacement multiplier may be a simple machine, such as a wheel, pulley, lever, and/or the like. For example, the displacement multiplier may double the displacement of release 451 relative to the displacement of trigger 461. In other words, the displacement multiplier may cause release 451 to travel two (2) inches for every one (1) inch of trigger 461 travel. Moreover, any suitable ratio of displacement between release 451 and trigger 461 is in accordance with the present disclosure.

In an embodiment, trigger 461 is actuated to release tab 461A allowing engagement portion 460B to slide off a portion of handle 410 as sock removal mechanism 460 is removed from handle 410, as shown in FIG. 5E. The actuation of trigger 461 causes release 451 to displace and uncouple the distal end of sock 450. Sock 450 and release 451 may then retract from a medical device preparing it for deployment.

Thus, the medical device delivery systems described herein provides an effective, lockable system capable of delivering medical devices to a human patient's vasculature and removing the sock from the medical device to allow for deployment.

Finally, the present invention has been described above with reference to a number of exemplary embodiments. It should be appreciated that the particular embodiments shown and described herein are illustrative of the invention and its best mode and are not intended to limit in any way the scope of the invention. Those skilled in the art having read this disclosure will recognize that changes and modifications may be made to the exemplary embodiments without departing from the scope of the present invention. For example, various aspects and embodiments of this invention may be used to provide other methods of treatment, such as drug eluting stents, and/or for imaging purposes, and to provide various methods of treatment to humans and other mammals alike. Although certain preferred aspects of the invention are described herein in terms of exemplary embodiments, such aspects of the invention may be achieved through any number of suitable means now known or hereafter devised. Accordingly, these and other changes or modifications are intended to be included within the scope of the present invention.

What is claimed is:

1. A medical device delivery system, comprising:
   a handle including a body, a removal mechanism removably coupled to the body, and a movable component maintained by the body and configured to be actuated to provide an input;
   a catheter coupled to the handle;
   an implantable medical device coupled to the catheter;
   a constraint including a sock that is configured to cover the medical device, the constraint extending through the body of the handle and being coupled to the removal mechanism such that the sock is retractable from covering the implantable medical device in response to the removal mechanism being separated from the handle;
   a release that is distinct from the constraint and coupled to the removal mechanism such that the release is retractable relative to the constraint in response to the removal mechanism being separated from the handle;
   the removal mechanism comprising a locking mechanism, the locking mechanism configured to engage the moveable component to prevent actuation of the moveable component prior to removal of the removal mechanism from the body, wherein the movable component is actuatable after removal of the locking mechanism by removing the removal mechanism from the body, and
   wherein the release is configured to open a distal end of the sock in response to the removal mechanism being separated from the handle and the release being retracted relative to the sock.

2. The medical device delivery system of claim 1, wherein the movable component is a rotatable component.

3. The medical device delivery system of claim 1, wherein the catheter is configured to receive the input from the moveable component.

4. The medical device delivery system of claim 1, wherein the medical device is configured to receive the input from the moveable component.

* * * * *